(12) United States Patent
Berthon-Jones et al.

(10) Patent No.: US 8,220,457 B2
(45) Date of Patent: Jul. 17, 2012

(54) ADMINISTRATION OF CPAP TREATMENT PRESSURE IN PRESENCE OF APNEA

(75) Inventors: Michael Berthon-Jones, Leonay (AU); Steven Paul Farrugia, Lugarno (AU)

(73) Assignee: ResMed Limited (AU)

( * ) Notice: Subject to any disclaimer, the term of this patent is extended or adjusted under 35 U.S.C. 154(b) by 565 days.

(21) Appl. No.: 12/250,188

(22) Filed: Oct. 13, 2008

(65) Prior Publication Data

US 2009/0038617 A1 Feb. 12, 2009

Related U.S. Application Data

(63) Continuation of application No. 11/237,278, filed on Sep. 28, 2005, which is a continuation of application No. 10/958,854, filed on Oct. 5, 2004, now Pat. No. 6,988,498, which is a continuation of application No. 10/281,743, filed on Oct. 28, 2002, now Pat. No. 6,817,361, which is a continuation-in-part of application No. 09/008,743, filed on Jan. 19, 1998, now Pat. No. 6,367,474.

(30) Foreign Application Priority Data

Nov. 7, 1997 (AU) .......................... PP0269

(51) Int. Cl.
*A61M 16/00* (2006.01)
*A61M 15/00* (2006.01)
(52) U.S. Cl. ......... 128/204.23; 128/200.24; 128/204.18; 128/204.21
(58) Field of Classification Search ............. 128/200.24, 128/204.18, 204.21, 204.23
See application file for complete search history.

(56) References Cited

U.S. PATENT DOCUMENTS

| | | |
|---|---|---|
| 3,817,246 A | 6/1974 | Weigl |
| 3,903,875 A | 9/1975 | Hughes |
| 3,932,054 A | 1/1976 | McKelvey |
| 3,985,467 A | 10/1976 | Lefferson |
| 4,387,722 A | 6/1983 | Kearns |
| 4,448,058 A | 5/1984 | Jaffe et al. |
| 4,499,914 A | 2/1985 | Schebler |
| 4,630,614 A | 12/1986 | Atlas |
| 4,686,999 A | 8/1987 | Snyder et al. |
| 4,795,314 A | 1/1989 | Prybella et al. |
| 4,823,788 A | 4/1989 | Smith et al. |
| 4,827,922 A | 5/1989 | Champain et al. |
| 4,870,960 A | 10/1989 | Hradek |
| 4,915,103 A | 4/1990 | Visveshwara et al. |

(Continued)

FOREIGN PATENT DOCUMENTS

EP 0651971 10/2010

*Primary Examiner* — Annettte Dixon
(74) *Attorney, Agent, or Firm* — Lerner, David, Littenberg, Krumholz & Mentlik, LLP

(57) ABSTRACT

A method and CPAP apparatus for automatically adjusting a continuous positive airway treatment pressure delivered to a patient responds in different manners according to the type of breathing problem. If a respiratory event is an apnea at a treatment pressure below a first value, then the treatment pressure is increased in one manner. If the respiratory event is a partial upper airway obstruction at a treatment pressure below a second value, then the treatment pressure is increased in a different manner; where the first pressure value is less than the second pressure value. In particular, obstructive and central apneas are treated differently by the apparatus.

12 Claims, 6 Drawing Sheets

U.S. PATENT DOCUMENTS

| | | |
|---|---|---|
| 4,944,310 A | 7/1990 | Sullivan |
| 4,957,107 A | 9/1990 | Sipin |
| 5,105,354 A | 4/1992 | Nishimura |
| 5,134,995 A | 8/1992 | Gruenke et al. |
| 5,199,424 A | 4/1993 | Sullivan |
| 5,203,343 A | 4/1993 | Axe |
| 5,245,995 A | 9/1993 | Sullivan |
| 5,259,373 A | 11/1993 | Gruenke |
| 5,261,397 A * | 11/1993 | Grunstein ................ 128/204.18 |
| 5,293,864 A | 3/1994 | McFadden |
| 5,438,980 A | 8/1995 | Phillips |
| 5,443,075 A | 8/1995 | Holscher |
| 5,448,996 A | 9/1995 | Bellin et al. |
| 5,458,137 A * | 10/1995 | Axe et al. ................ 128/204.23 |
| 5,522,382 A | 6/1996 | Sullivan |
| 5,537,997 A | 7/1996 | Mechlenberg et al. |
| 5,540,220 A | 7/1996 | Gropper |
| 5,549,106 A | 8/1996 | Gruenke |
| 5,551,419 A | 9/1996 | Froehlich |
| 5,570,682 A | 11/1996 | Johnson |
| 5,630,411 A | 5/1997 | Holscher |
| 5,645,053 A | 7/1997 | Remmers |
| 5,645,054 A | 7/1997 | Cotner et al. |
| 5,660,171 A | 8/1997 | Kimm et al. |
| 5,704,345 A | 1/1998 | Berthon-Jones |
| 5,740,795 A | 4/1998 | Brydon |
| 5,765,554 A * | 6/1998 | Somerson et al. ....... 128/205.23 |
| 5,803,066 A * | 9/1998 | Rapoport et al. ........ 128/204.23 |
| 5,953,713 A | 9/1999 | Behbehani et al. |
| 5,970,975 A | 10/1999 | Estes et al. |
| 6,085,747 A | 7/2000 | Axe et al. |
| 6,135,106 A | 10/2000 | Dirks et al. |
| 6,138,675 A | 10/2000 | Berthon-Jones |
| 6,363,933 B1 * | 4/2002 | Berthon-Jones ......... 128/204.23 |
| 6,367,474 B1 | 4/2002 | Berthon-Jones et al. |
| 6,398,739 B1 | 6/2002 | Sullivan |
| 6,502,572 B1 | 1/2003 | Berthon-Jones et al. |
| 6,635,021 B1 | 10/2003 | Sullivan |
| 6,817,361 B2 | 11/2004 | Berthon-Jones et al. |
| 6,988,498 B2 | 1/2006 | Berthon-Jones et al. |
| 2006/0021618 A1 | 2/2006 | Berthon-Jones et al. |

* cited by examiner

ADMINISTRATION OF CPAP TREATMENT PRESSURE IN PRESENCE OF APNEA

This application is a continuation of application Ser. No. 11/237,278 filed Sep. 28, 2005, which is a continuation of 10/958,854, filed Oct. 5, 2004, now U.S. Pat. No. 6,988,498 issued Jan. 24, 2006, which is a continuation of 10/281,743, filed Oct. 28, 2002, now U.S. Pat. No. 6,817,361, issued Nov. 16, 2004, which claims the priority date of U.S. Pat. No. 6,502,572, issued Jan. 7, 2003, which is a Continuation-in-part of 09/008,743, filed Jan. 19, 1998, now U.S. Pat. No. 6,367,474, issued Apr. 9, 2002, entitled "Administration of CPAP Treatment Pressure in Presence of Apnea" which claims priority to Australian application No. PP0269 filed Nov. 7, 1997.

FIELD OF THE INVENTION

This invention relates to the administration of continuous positive airway pressure (CPAP) treatment for partial or complete upper airway obstruction.

BACKGROUND OF THE INVENTION

In the Sleep Apnea syndrome a person stops breathing during sleep. Cessation of airflow for more than 10 seconds is called an "apnea". Apneas lead to decreased blood oxygenation and thus to disruption of sleep. Apneas are traditionally (but confusingly) categorized as either central, where there is no respiratory effort, or obstructive, where there is respiratory effort. With some central apneas, the airway is open, and the subject is merely not attempting to breathe. Conversely, with other central apneas and all obstructive apneas, the airway is closed. The occlusion is usually at the level of the tongue or soft palate. The airway may also be partially obstructed (i.e., narrowed or partially patent). This also leads to decreased ventilation (hypopnea), decreased blood oxygenation and disturbed sleep.

The common form of treatment of these syndromes is the administration of Continuous Positive Airway Pressure (CPAP). The procedure for administering CPAP treatment has been well documented in both the technical and patent literature. An early description can be found in U.S. Pat. No. 4,944,310 (Sullivan). Briefly stated. CPAP treatment acts as a pneumatic splint of the airway by the provision of a positive pressure usually in the range 4-20 cm $H_2O$. The air is supplied to the airway by a motor driven blower whose outlet passes via an air delivery hose to a nose (or nose and/or mouth) mask sealingly engaged to a patient's face. An exhaust port is provided in the delivery tube proximate to the mask. The mask can take the form of a nose and/or face mask or nasal prongs, pillows or cannulae.

Various techniques are known for sensing and detecting abnormal breathing patterns indicative of obstructed breathing. U.S. Pat. No. 5,245,995 (Sullivan et al.), for example, generally describes how snoring and abnormal breathing patterns can be detected by inspiration and expiration pressure measurements made while a subject is sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to, ideally, subvert the occurrence of the obstructive episodes and the other forms of breathing disorder.

Automatic detection of partial upper airway obstruction and pre-emptive adjustment of nasal CPAP pressure works to prevent frank obstructive apneas in the majority of subjects with obstructive sleep apnea syndrome. However, some subjects with severe disease progress directly from a stable open upper airway to a closed airway apnea with complete airway closure, with little or no intervening period of partial obstruction. Therefore it is useful for an automatically adjusting CPAP system to also respond to a closed airway apnea by an increase in CPAP pressure. However, it is not desirable to increase CPAP pressure in response to open airway apneas, firstly because this leads to an unnecessarily high pressure and secondly because the high pressure can reflexly cause yet further open airway apneas, leading to a vicious circle of pressure increase.

One method for distinguishing open airway apneas (requiring no increase in pressure) from closed airway apneas (requiring a pressure increase) is disclosed in commonly owned European Publication No. 0 651 971 A1 (corresponding to U.S. Pat. No. 5,704,345). During an apnea, the mask pressure is modulated at 4 Hz with an amplitude of the order of 1 $cmH_2O$, the induced airflow at 4 Hz is measured, and the conductance of the airway is calculated. A high conductance indicates an open airway. This 'forced oscillation method' requires the ability to modulate the mask pressure at 4 Hz, which increases the cost of the device. Furthermore, the method does not work in the presence of high leak, and can falsely report that the airway is closed if the subject has a high nasal or intrapulmonary resistance.

The present invention is directed to overcoming or at least ameliorating one or more of the foregoing disadvantages in the prior art.

SUMMARY OF THE INVENTION

Therefore, the invention discloses a method for the administration of CPAP treatment pressure comprising the steps of:
  supplying breathable gas to the patient's airway at a treatment pressure;
  determining a measure of respiratory airflow; and
  determining the occurrence of an apnea from a reduction in the measure of respiratory airflow below a threshold, and, if having occurred
    (i) determining the duration of the apnea; and
    (ii) increasing the treatment pressure by an amount which is an increasing function of the duration of the apnea, and a decreasing function of the treatment pressure immediately before the apnea.

The invention further discloses CPAP treatment apparatus comprising:
  a controllable flow generator operable to produce breathable gas at a pressure elevated above atmosphere;
  a gas delivery tube coupled to the flow generator;
  a patient mask coupled to the tube to receive said breathable gas from the flow generator and provide said gas, at a desired treatment pressure, to the patient's airway;
  a controller operable to receive input signals and to control operation of said flow generator and hence the treatment pressure; and
  sensor means located to sense patient respiratory airflow and generate a signal input to the controller from which patient respiratory airflow is determined;
  and wherein said controller is operable to determine the occurrence of an apnea from a reduction in said respiratory airflow below a threshold, and if having occurred, to determine the duration of said apnea and cause said flow generator to increase CPAP treatment pressure by an amount that is an increasing function of said apnea duration, and a decreasing function of the treatment pressure immediately prior to said apnea.

The invention yet further provides CPAP treatment apparatus comprising:

a controllable flow generator operable to produce breathable gas to be provided to a patient at a treatment pressure elevated above atmosphere; and a controller operable to receive input signals representing patient respiratory airflow, and to control operation of said flow generator and hence the treatment pressure;

and wherein said controller is operable to determine the occurrence of an apnea from a reduction in said respiratory airflow below a threshold, and, if having occurred, to determine the duration of said apnea and cause said flow generator to increase CPAP treatment pressure by an amount that is an increasing function of said apnea duration, and a decreasing function of the treatment pressure immediately prior to said apnea.

Preferably, the increase in treatment pressure is zero if the treatment pressure before the apnea exceeds a pressure threshold. The increase in pressure below the pressure threshold can be an increasing function of the duration of the apnea, multiplied by the difference between the pressure threshold and the current treatment pressure. Further, the increasing function of apnea duration is linear on apnea duration. Advantageously, said increasing function of apnea duration is zero for zero apnea duration, and exponentially approaches an upper limit as apnea duration goes to infinity.

The occurrence of an apnea can be determined by calculating the RMS respiratory airflow over a short time interval, calculating the RMS respiratory airflow over a longer time interval, and declaring an apnea if the RMS respiratory airflow over the short time interval is less than a predetermined fraction of the RMS respiratory airflow over the longer time interval. There also can be the further step or action of reducing the treatment pressure towards an initial treatment pressure in the absence of a further apnea.

In a preferred form, said sensor means can comprise a flow sensor, and said controller derives respiratory airflow therefrom.

In one preferred form said initial treatment pressure is 4 $cmH_2O$, said measure of respiratory airflow is the two second moving average RMS airflow, and said threshold is 25% of the RMS airflow over the preceding 5 minutes. In this preferred form no increase in pressure is made for apneas of less than 10 seconds duration, or for apneas where the treatment pressure immediately prior to the apnea is more than 10 $cmH_2O$, but otherwise, the lower the treatment pressure immediately prior to the apnea, and the longer the apnea, the greater the increase in treatment pressure, up to a maximum of 8 $cmH_2O$ per minute of apnea. In this preferred form, if there is no apnea the treatment pressure is gradually reduced towards the initial minimum pressure with a time constant of 20 minutes.

The method and apparatus can advantageously be used in concert with one or more other methods for determining the occurrence of partial upper airway obstruction, such that either complete or partial upper airway obstruction can lead to an increase in pressure, but once there is no longer either complete or partial obstruction, the pressure will gradually reduce towards the initial minimum pressure.

In one particularly preferred form, partial obstruction is detected as either the presence of snoring, or the presence of characteristic changes in the shape of the inspiratory flow-vs-time curve indicative of inspiratory airflow limitation.

The method and apparatus can also advantageously be used in concert with the 'forced oscillation method' for measuring airway patency (referred to above as European Publication No. 0 651 971 A1, U.S. Pat. No. 5,704,345 whose disclosure is hereby incorporated by reference), in which the CPAP pressure is modulated with an amplitude of for example 1 $cmH_2O$ at 4 Hz, the induced airflow at 4 Hz is measured, the conductance of the airway calculated by dividing the amplitude of the induced airflow by the pressure modulation amplitude, and the additional requirement imposed that the treatment pressure is only increased if said conductance is greater than a threshold.

Closed airway apneas are most likely to occur at low CPAP pressures, because high CPAP pressures splint the airway partially or completely open whereas pressure-induced open airway apneas are most likely to occur at high CPAP pressures, at least partially because high CPAP pressures increase lung volume and thereby stimulate the Hering-Breuer reflex, leading to inhibition of breathing. Therefore, the lower the existing CPAP pressure, the more likely an apnea is to be of the closed airway variety, and the more appropriate it is to increase the treatment pressure, whereas the higher the existing CPAP pressure, the more likely an apnea is to be of the open airway variety, and the more appropriate it is to leave the CPAP pressure unchanged. Generally apneas of less than 10 seconds duration are regarded as non-pathological, and there is no need to increase CPAP pressure, whereas very long apneas require treatment. The present invention will correctly increase the CPAP pressure for most closed airway apneas, and correctly leave the CPAP pressure unchanged for most open airway apneas.

The present invention can be combined with an independent pressure increase in response to indicators of partial upper airway obstruction such as snoring or changes in shape of the inspiratory flow-time curve. In this way it is possible in most subjects to achieve pre-emptive control of the upper airway, with pressure increases in response to partial upper airway obstruction preventing the occurrence of closed airway apneas. In the minority of subjects in whom pre-emptive control is not achieved, this combination will also correctly increase the CPAP pressure in response to those closed airway apneas that occur at low CPAP pressure without prior snoring or changes in the shape of the inspiratory flow-time curve. Furthermore, the combination will avoid falsely increasing the CPAP pressure in response to open airway apneas induced by high pressure.

Some open airway apneas can occur at low pressure. By combining the forced oscillation method with the present invention, with the additional requirement that there be no increase in pressure if the forced oscillation method detects an open airway, false increases in pressure in response to open airway apneas at low pressure will be largely avoided.

BRIEF DESCRIPTION OF THE DRAWINGS

Embodiments of the invention will now be described with reference to the accompanying drawings, in which.

DETAILED DESCRIPTION OF THE PREFERRED EMBODIMENTS

Figure 1:
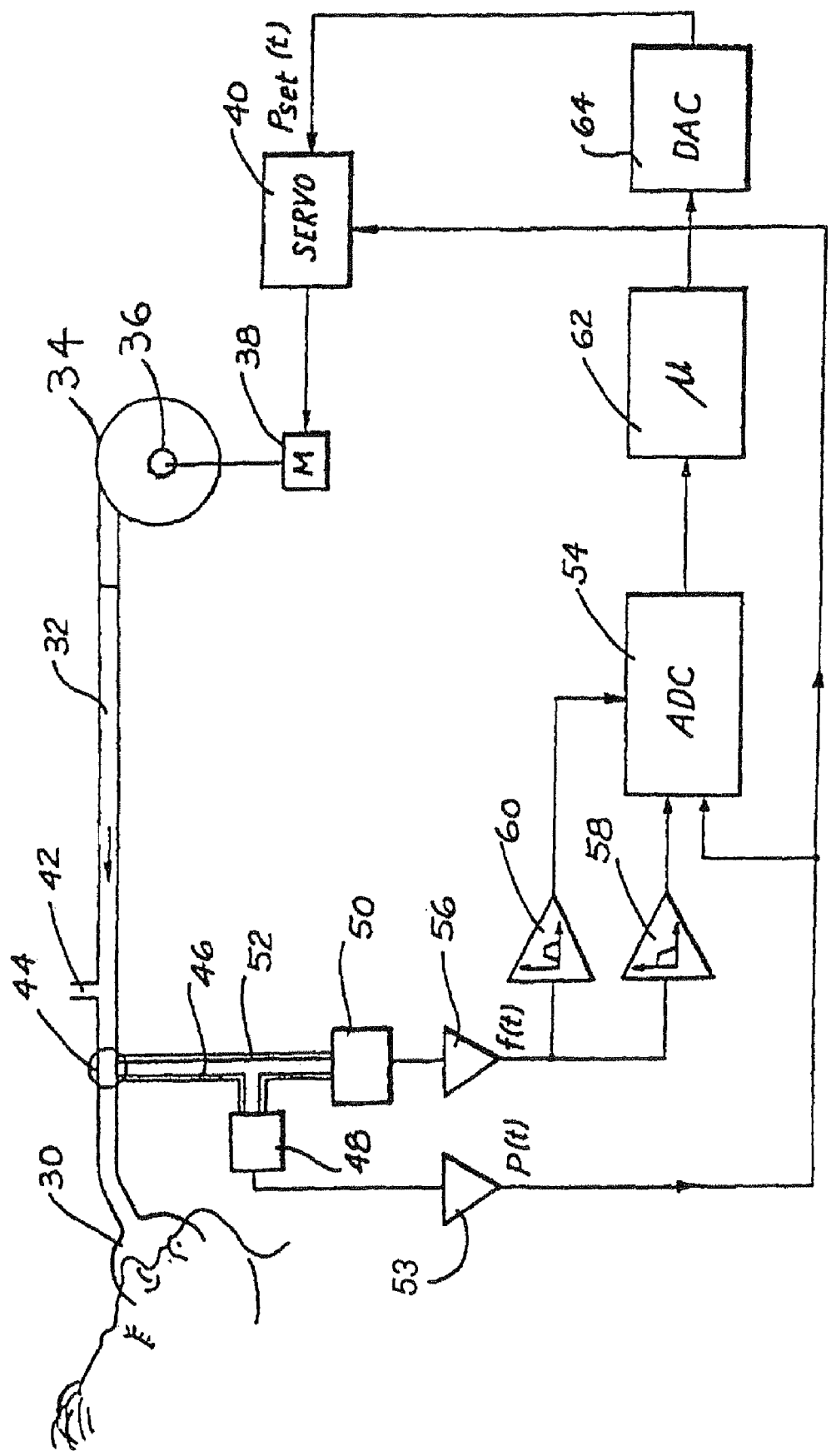
FIG. 1 shows, in diagrammatic form, apparatus embodying the invention.

FIG. 1 shows, in diagrammatic form, CPAP apparatus in accordance with one embodiment. A mask 30, whether either a nose mask and/or a face mask, is sealingly fitted to a patient's face. Breathable gas in the form of fresh air, or oxygen enriched air, enters the mask 30 by flexible tubing 32 which, in turn is connected with a motor driven turbine 34 to which there is provided an air inlet 36. The motor 38 for the turbine is controlled by a motor-servo unit 40 to commence, increase or decrease the pressure of air supplied to the mask 30 as CPAP treatment. The mask 30 also includes an exhaust port 42 that is close to the junction of the tubing 34 with the mask 30.

Interposed between the mask 30 and the exhaust 42 is a linear flow-resistive element 44. In practice, the distance between mask 30 and exhaust 42, including flow resistive element 44 is very short so as to minimize deadspace volume. The mask side of the flow-resistive element 44 is connected by a small bore tube 46 to a mask pressure transducer 48 and to an input of a differential pressure transducer 50. Pressure at the other side of the flow-resistive element 44 is conveyed to the other input of the differential pressure transducer 50 by another small bore tube 52.

The mask pressure transducer 48 generates an electrical signal in proportion to the mask pressure, which is amplified by amplifier 53 and passed both to a multiplexer/ADC unit 54 and to the motor-servo unit 40. The function of the signal provided to the motor-servo unit 40 is as a form of feedback to ensure that the actual mask static pressure is controlled to be closely approximate to the set point pressure.

The differential pressure sensed across the linear flow-resistive element 44 is output as an electrical signal from the differential pressure transducer 50, and amplified by another amplifier 56. The output signal from the amplifier 56 therefore represents a measure of the mask airflow. The linear flow-resistive element 44 can be constructed using a flexible-vaned iris. Alternatively, a fixed orifice can be used, in which case a linearization circuit is included in amplifier 52, or a linearization step such as table lookup included in the operation of controller 62.

The output signal from the amplifier 56 is low-pass filtered by the low-pass filter 58, typically with an upper limit of 10 Hz, in order to remove non-respiratory noise. The amplifier 56 output signal is also bandpassed by the bandpass filter 60, and typically in a range of 30-100 Hz to yield a snoring signal. The outputs from both the low-pass filter 58 and the bandpass filter 60 are provided to the digitizer (ADC) unit 54. The digitized respiratory airflow (FLOW), snore, and mask pressure ($P_{mask}$) signals from ADC 54 are passed to a controller 62 typically constituted by a micro-processor based device also provided with program memory and data processing storage memory.

The controller 62 outputs a pressure request signal which is converted to a voltage by DAC 64, and passed to the motor-servo unit 40. This signal therefore represents the set point pressure $P_{set}(t)$ to be supplied by the turbine 34 to the mask 30 in the administration of CPAP treatment. The controller 62 is programmed to perform a number of processing functions, as presently will be described.

As an alternative to the mask pressure transducer 48, a direct pressure/electrical solid state transducer (not shown) can be mounted from the mask with access to the space therewithin, or to the air delivery tubing 32 proximate the point of entry to the mask 30.

Figure 2:
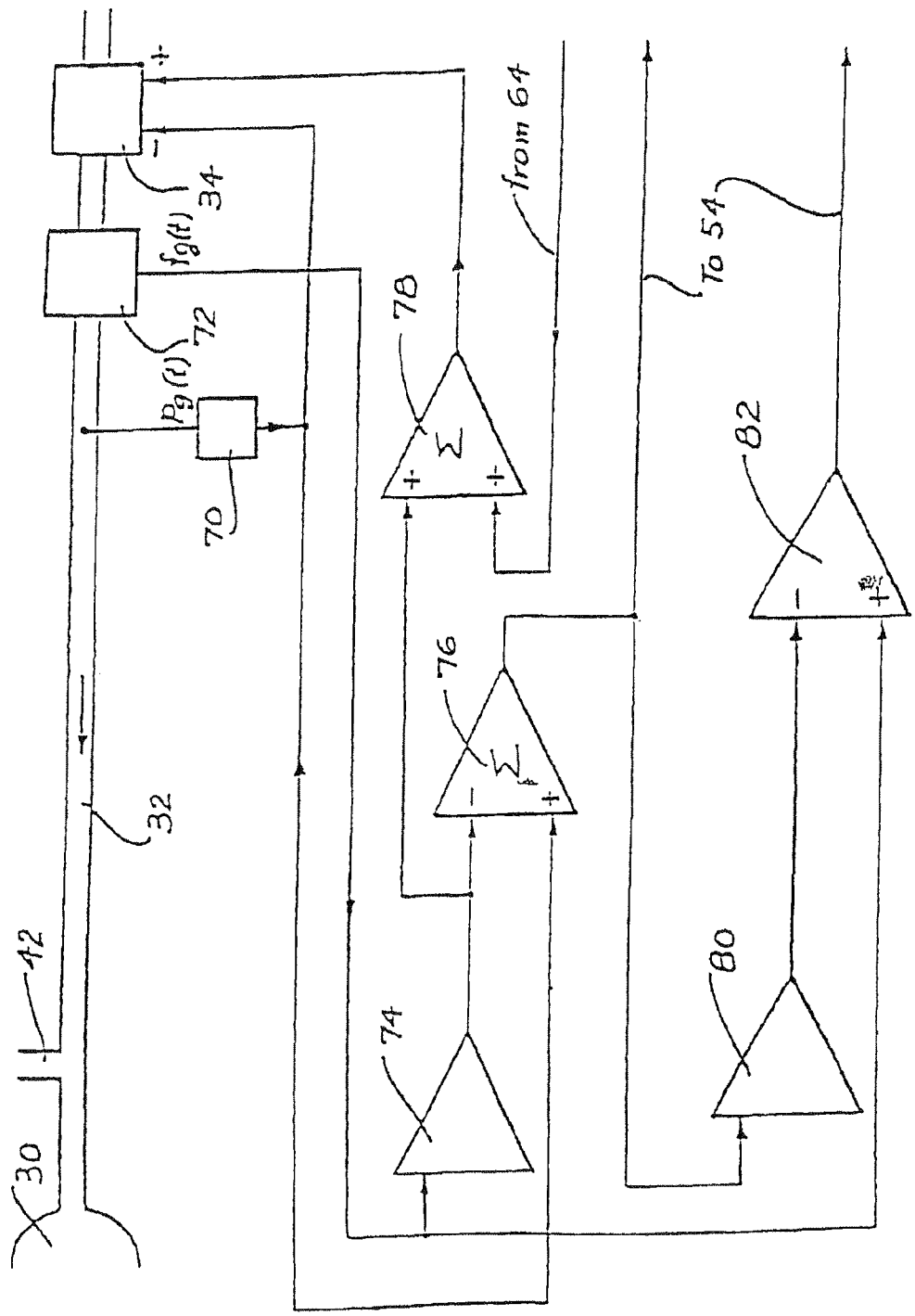
FIG. 2 shows an alternative arrangement of the apparatus of FIG. 1.

Further, it may not be convenient to mount the flow transducer 44 at or near the mask 30, nor to measure the mask pressure at or near the mask. An alternative arrangement, where the flow and pressure transducers are mounted at or near the air pressure generator (in the embodiment being the turbine 34) is shown in FIG. 2

The pressure $p_g(t)$ occurring at the-pressure generator 34 outlet is measured by a pressure transducer 70. The flow $f_g(t)$ through tubing 32 is measured with flow sensor 72 provided at the output of the turbine 34. The pressure loss along tubing 32 is calculated in element 74 from the flow through the tube $f_g(t)$, and a knowledge of the pressure-flow characteristic of the tubing, for example by table lookup. The pressure at the mask $p_m$ is then calculated in subtraction element 76 by subtracting the tube pressure loss from $p_g(t)$.

The pressure loss along tube 32 is then added to the desired set pressure at the mask $p_{set}(t)$ in summation element 78 to yield the desired instantaneous pressure at the pressure generator 34. Preferably, the controller of the pressure generator 34 has a negative feedback input from the pressure transducer 70, so that the desired pressure from step 78 is achieved more accurately. The flow through the exhaust 42 is calculated from the pressure at the mask (calculated in element 76) from the pressure-flow characteristic of the exhaust in element 80, for example by table lookup. Finally, the mask flow is calculated by subtracting the flow through the exhaust 42 from the flow through the tubing 32, in subtraction element 82

The methodology put into place by the controller 62 will now be described. In a first embodiment, there is a pressure response to apneas, but not to indicators of partial obstruction, and therefore snore detection bandpass filter 60 is not required.

An initial CPAP treatment pressure, typically 4 $cmH_2O$, is supplied to the subject. The FLOW signal is processed to detect the occurrence of an apnea (as will presently be discussed) and, at the same time the $P_{mask}$ signal is recorded. When it is determined that an apnea has occurred its duration is recorded. At the same time $P_{mask}$ is compared against a pressure threshold, $P_u$. If $P_{mask}$ is at or above $P_u$ the controller will act to maintain or reduce that pressure. If, on the other hand, $P_{mask}$ is below $P_u$, the controller will act to increase the treatment pressure by an amount $\Delta P$.

In a preferred form, $\Delta P$ is determined as follows $$\Delta P = [P_u - P] f(t_a) \quad (1)$$

where $\Delta P$ is the change in pressure ($cmH_2O$)

$P_u$ is the pressure threshold, which in an embodiment can be 10 $cmH_2O$

P is the current treatment pressure immediately before the apnea ($cmH_2O$)

$t_a$ is the apnea duration(s)

Figure 3:
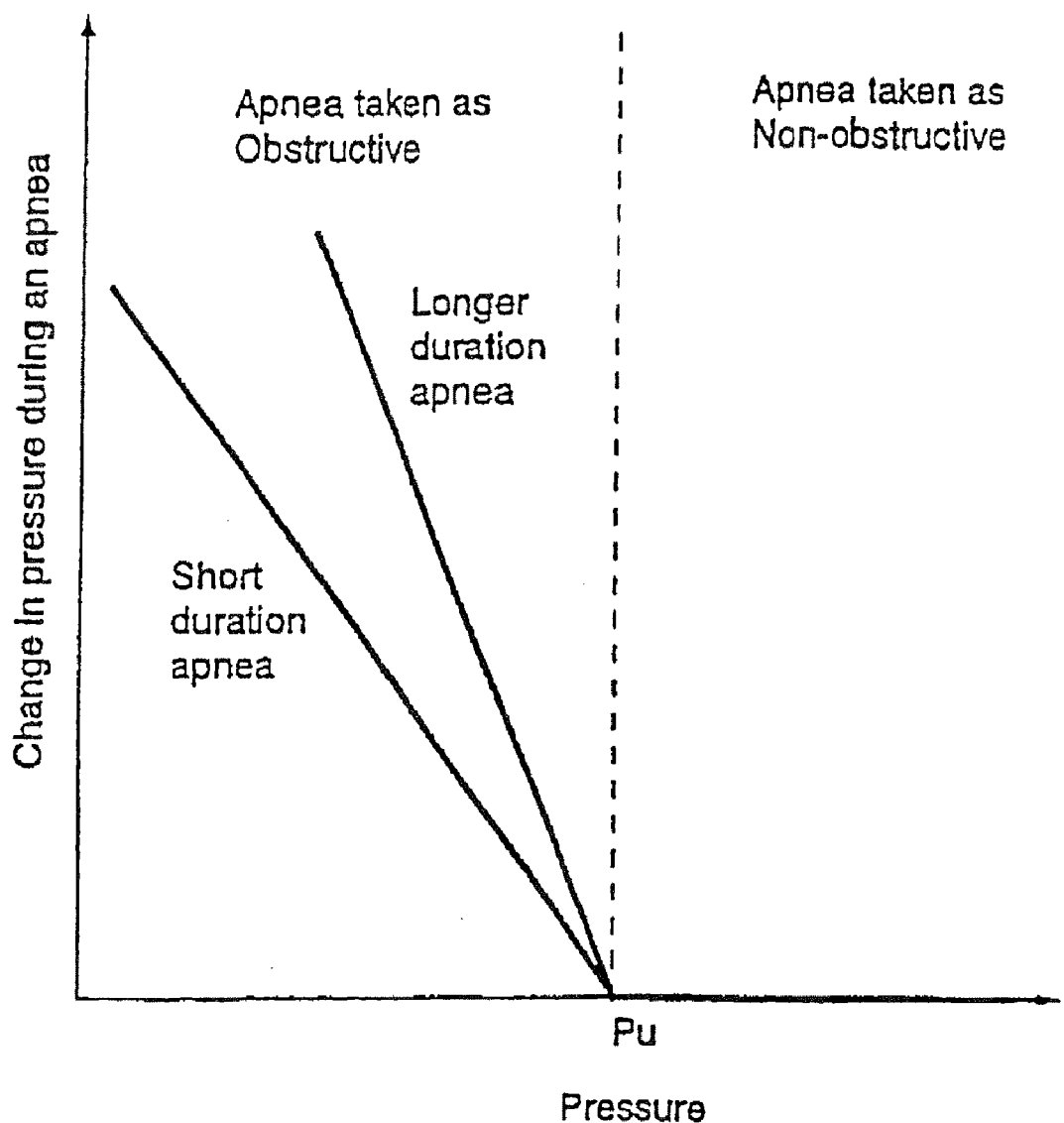
FIG. 3 shows a plot of two pressure change characteristics as a function of apnea duration.

$f(t_a)$ is a function that is a monotonically increasing function of $t_a$, zero for $t_a=0$ FIG. 3 is a graphical representation of equation (1), showing a region below $P_u$ where it is taken that an apnea is obstructive and demonstrating two cases of the $\Delta P$ characteristic as a function of apnea duration (ie short and longer) such that $\Delta P$ is an increasing function of apnea duration and a decreasing function of the current treatment pressure. Above $P_u$, it is taken that the apnea is non-obstructive, and $\Delta P$ is held to be zero for all values of the current treatment pressure.

$$1f(t_a) = rt_a P_{max} \quad (2)$$

One form of the function $f(t_a,a)$ is:

In one embodiment the parameters can be:

$$r = 0.13 \text{ cmH}_2O \cdot s^{-1}$$

$$\Delta P_{max} = 6 \text{ cmH}_2O$$

Another form of the function $f(t_a)$ is:

$$f(t_a,a) = 1 - \exp(-k t_a) \quad (3)$$

In one embodiment the parameter can be $k=0.02 \text{ s}^{-1}$

Figure 4:
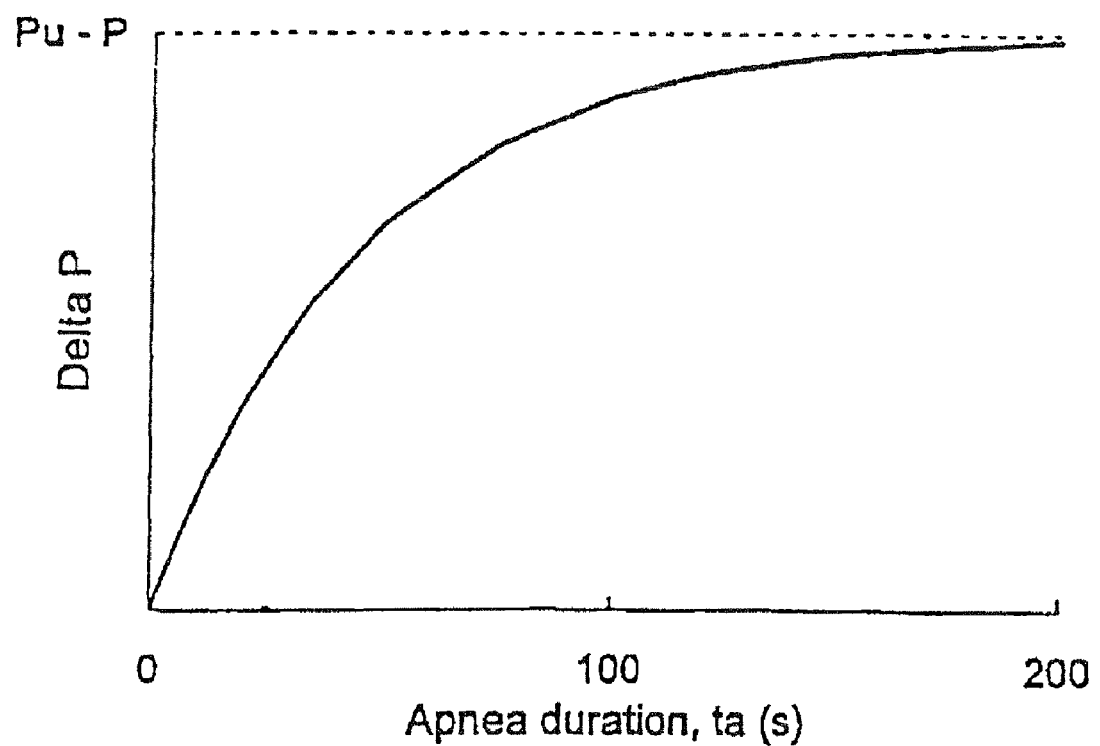
FIG. 4 shows a plot of the apnea duration function.

FIG. 4 is a graphical representation of equation (3) for the parameters given above.

The controller 62 implements the foregoing methodology using the following pseudo-code.

Set apnea duration to zero
Clear "start of breath" flag
Set initial CPAP pressure to 4 cmH_2O.
Set maximum delta pressure due to apnea to 6 cmH_2O.
Set top roll-off pressure to initial CPAP pressure plus maximum delta pressure due to apnea.
REPEAT
Sample mask airflow (in L/sec) at 50 Hz.
Calculate mask leak as mask airflow low pass filtered with a time constant of 10 seconds.
Check for presence and duration of any apnea
Check for start of breath.
IF start of breath flag set:
IF apnea duration greater than 10 seconds AND current CPAP pressure less than top roll-off pressure:
Set delta pressure for this apnea to (top roll-off pressure—current CPAP pressure)/maximum delta pressure due to apnea times 8 cmH_2O per minute of apnea duration.
Add delta pressure for this apnea to total delta pressure due to apnea, and truncate to maximum delta pressure due to apnea.
Reset apnea duration to zero.
ELSE
Reduce total delta pressure due to apnea with a time constant of 20 minutes.
End
Set CPAP pressure to initial CPAP pressure plus total delta pressure due to apnea.
Clear start of breath flag.
END
END This implementation is suitable for subjects in whom obstructive apneas are controlled at a CPAP pressure of less than 10 cmH_2O. Increasing the maximum delta pressure due to apnea from 6 cmH_2O to 10 cmH_2O would permit the prevention of obstructive apneas in the majority of subjects, in exchange for an increase in undesirable pressure increases due to open airway apneas.

Figure 5:
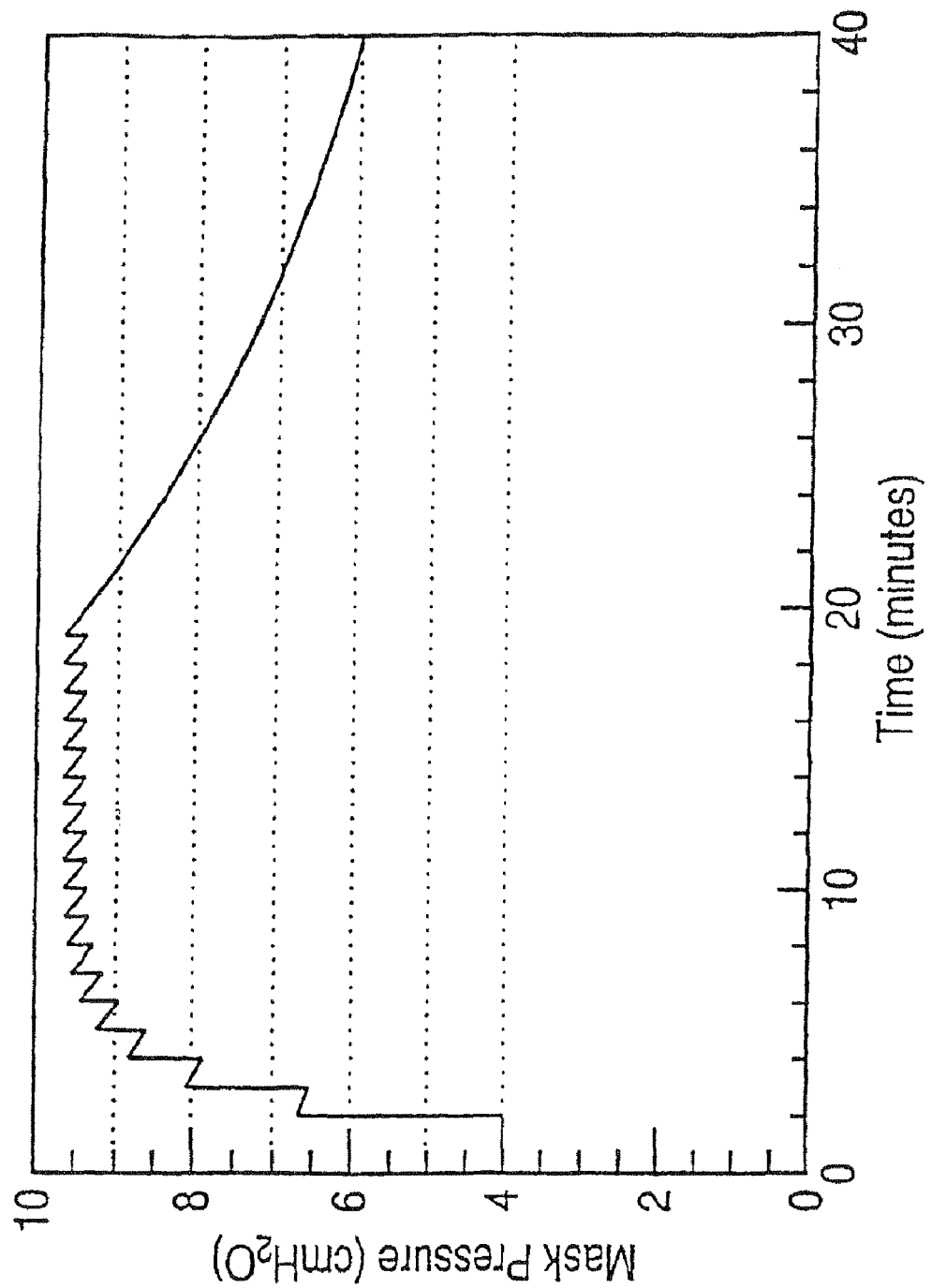
FIG. 5 shows a graph of CPAP treatment pressure versus time for a preferred embodiment of the invention.

The procedure "Check for presence and duration of any apnea" can be implemented using the following pseudocode:

Calculate 2 second RMS airflow as the RMS airflow over the previous 2 seconds.
Calculate longterm average RMS airflow as the 2 second RMS airflow, low pass filtered with a time constant of 300 seconds.
IF 2 second RMS airflow is less than 25% of longterm average RMS airflow:
Mark apnea detected and increment apnea duration by {fraction (1/50)} second.
END The procedure, "Check for start of breath" is implemented by the following pseudocode:

IF respiratory airflow is inspiratory AND respiratory airflow on previous sample was not inspiratory.
Set "start of breath" flag.
END FIG. 5 shows the above method and apparatus in operation. The mask 30 was connected to a piston driven breathing simulator set to a normal respiratory rate and depth, and programmed to introduce a 20 second apnea once per minute from the 2nd minute to the 20th minute. In operation, the pressure remained at the initial pressure of 4 cmH_2O until the first apnea, which led to a brisk increase in mask pressure. The pressure then decayed slightly during the subsequent 40 seconds of normal breathing. Subsequent apneas produced smaller increments, and the mask pressure settled out to approximately 9.5 cmH_2O. In most actual patients, the number of apneas would reduce as the pressure increased. Because the pressure due to repetitive apneas cannot exceed 10 cmH_2O, and most pressure-induced open airway apneas occur at very high pressures typically above 10 cmH_2O, this algorithm will not falsely or needlessly increase pressure in response to most pressure-induced open airway apneas, thus avoiding a vicious cycle of high pressure leading to open airway apneas leading to yet further pressure increase.

The above embodiment can be considerably improved by the addition of independent pressure increases in response to partial upper airway obstruction indicated by the presence of snoring or changes in the shape of the inspiratory flow-vs-time curve. In the majority of subjects, in whom substantial periods of snoring or flow limitation exist prior to any closed airway apneas, the CPAP pressure will increase in response to said snoring and/or changes in the shape of the inspiratory flow-vs-time curve, to a sufficient level to largely eliminate severe partial obstruction, without any apneas of any kind occurring. In those subjects in whom closed airway apneas appear with little or no prior period of partial obstruction, the first few apneas will produce a brisk increase in CPAP pressure as previously discussed, and in general this will provide sufficient partial support to the airway to permit periods of detectable partial obstruction, preventing any further apneas from occurring.

This second embodiment is implemented using the following pseudocode.

Set initial CPAP pressure to 4 cmH_2O.
Set apnea duration to zero
Clear "start of breath" flag
REPEAT every {fraction (1/50)} of a second
Sample mask pressure (in cmH_2O), mask airflow (in L/sec), and snore (1 unit corresponds loosely to a typical snore).
Calculate mask leak as mask airflow low pass filtered with a time constant of 10 seconds.
Adjust snore signal for machine noise.
Check for presence and duration of any apnea.
Check for start of breath.
IF start of breath flag set:
IF apnea duration greater than 10 seconds AND current CPAP pressure less than 10 cmH_2O:
Set delta pressure for this apnea to (10−current CPAP pressure)/6 times 8 cmH_2O per minute of apnea duration.

Add delta pressure for this apnea to total delta pressure due to apnea, and truncate to 16 cmH.sub.2O
Reset apnea duration to zero.
ELSE
Reduce total delta pressure due to apnea with a time constant of 20 minutes.
END
Calculate flow limitation index.
Calculate flow limitation threshold.
IF flow limitation index is less than said threshold:
Set flow limitation delta pressure for this breath to 3 cmH.sub.2O times (threshold-flow limitation index).
Add flow limitation delta pressure for this breath to total delta pressure due to flow limitation, and truncate to 16 cmH.sub.2O.
ELSE
Reduce total delta pressure due to flow limitation with a time constant of 10 minutes.
END
Calculate mean snore for breath.
Calculate snore threshold.
IF mean snore exceeds said threshold:
set delta pressure due to snore for this breath to 3 cmH.sub.2O times (mean snore for this breath—threshold).
Add delta pressure due to snore for this breath to total delta pressure due to snore, and truncate to 16 cmH.sub.2O.
ELSE
Reduce total delta pressure due to snore with a time constant of 10 minutes.
END
Set CPAP pressure to 4 cmH.sub.2O plus total delta pressure due to apnea plus total delta pressure due to snore plus total delta pressure due to flow limitation, and truncate to 20 cmH.sub.2O.
Clear start of breath flag.
END
END In the above implementation, apneas can only cause the CPAP pressure to rise as far as 10 cmH.sub.2O, but subsequently, indicators of partial obstruction can increase the CPAP pressure to 20 cmH.sub.2O, which is sufficient to treat the vast majority of subjects.

The procedure "Adjust snore for machine noise" is described by the following pseudocode Machine noise=$K1$*mask pressure+$K2$*mask pressure squared+$K3$*mask flow+$K4$*time derivative of mask flow+$K5$*time derivative of mask pressure.

Adjusted snore signal=raw snore signal-machine noise.
where the constants $K1$ to $K5$ are determined empirically for any particular physical embodiment, and for a particular machine may be zero. In other embodiments, blower fan speed measured with a tachometer or pressure at the blower may be used instead of mask pressure.

The procedure "Calculate flow limitation index" is described by the following pseudocode:
Identify the inspiratory portion of the preceding breath
Note the duration of inspiration.
Calculate the mean inspiratory airflow.
For each sample point over said inspiratory portion, calculate a normalized inspiratory airflow by dividing the inspiratory airflow by the mean inspiratory airflow.
Identify a mid-portion consisting of those sample points between 25% and 75% of the duration of inspiration.
Calculate the flow limitation index as the RMS deviation over said mid-portion of (normalized inspiratory airflow−1)

Figure 6:
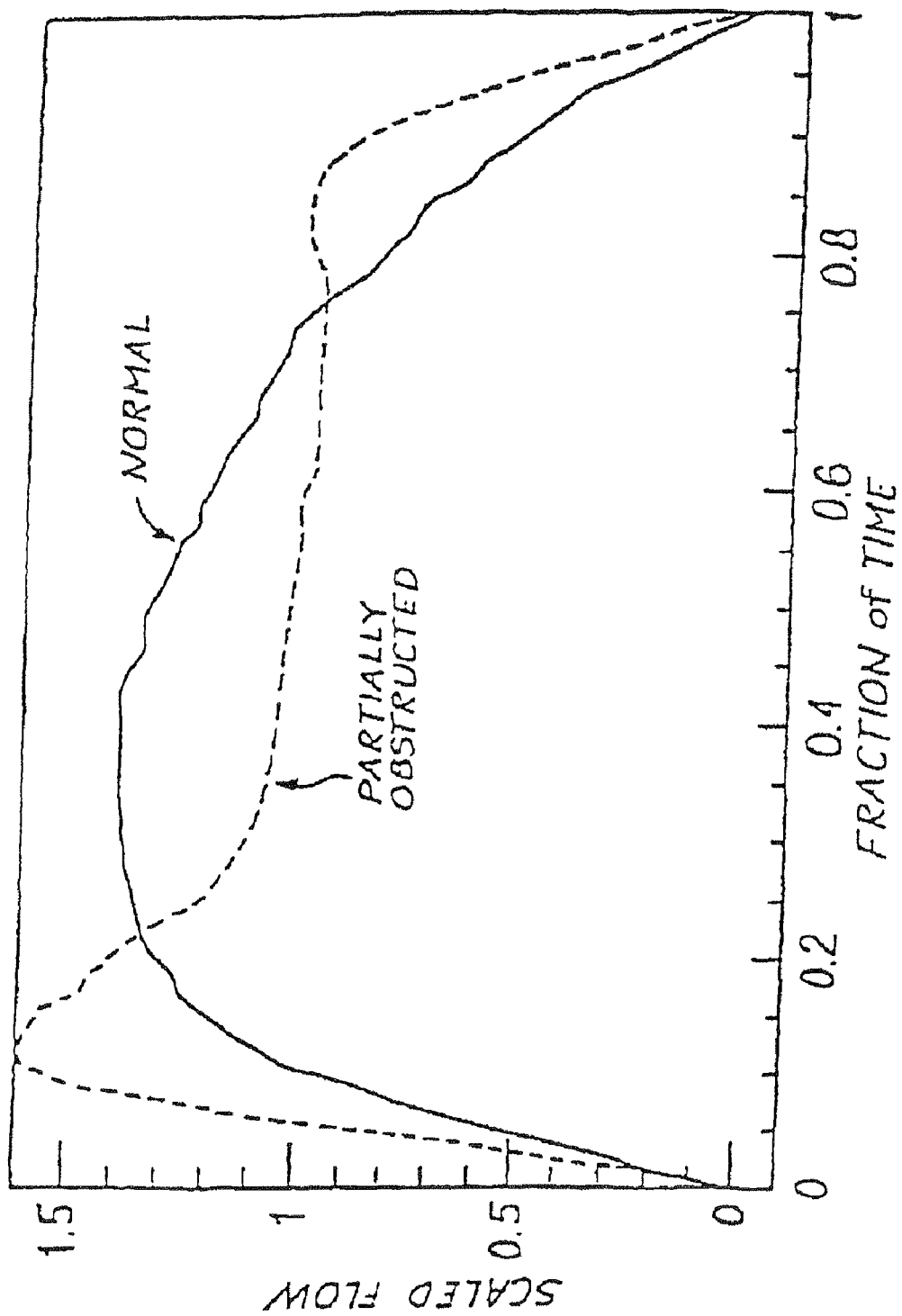
FIG. 6 shows a graph of scaled (normalized) air flow with time for normal and partially obstructed inspiration.

The logic of the above algorithm is as follows: partial upper airway obstruction in untreated or partially treated Obstructive Sleep Apnea syndrome, and the related Upper Airway Resistance syndrome, leads to mid-inspiratory flow limitation, as shown in FIG. 6, which shows typical inspiratory waveforms respectively for normal and partially obstructed breaths after scaling (normalizing) to equal mean amplitude and duration.

For a totally flow-limited breath, the flow amplitude vs. time curve would be a square wave and the RMS deviation would be zero. For a normal breath, the RMS deviation is approximately 0.2 units, and this deviation decreases as the flow limitation becomes more severe.

In some patients, it is not possible to prevent all upper airway obstruction, even at maximum pressure. In addition, there is a trade-off between the possible advantage of increasing the pressure in response to snoring and the disadvantage of increased side effects. This trade-off is implemented in procedure "calculate snore threshold" by looking up the snore threshold in the following table:

1 Pressure Threshold (cm H.sub.2O) (snore units)
Description <10 0.2 very soft 10-12 0.25 12-14 0.3 soft 14-16 0.4 16-18 0.6 moderate >18 1.8 loud For similar reasons, the procedure "calculate flow limitation threshold" sets the flow limitation threshold to a lower value corresponding to more severe flow limitation, if the pressure is already high or if there is a large leak:
IF mask leak is greater than 0.7 L/sec
set leak roll-off to 0.0
ELSE if mask leak is less than 0.3 L/sec
set leak roll-off to 1.0
ELSE
set leak roll-off to (0.7-mask leak)/0.4
END
Set pressure roll-off to (20-mask pressure)/16
Set flow limitation threshold to 0.15 times pressure roll-off times leak roll-off Some subjects will have occasional open airway apneas at sleep onset during stage 1 sleep and therefore at low pressure, and the above algorithm will incorrectly increase CPAP pressure in response to these events. However, such apneas are not usually repetitive, because the subject quickly becomes more deeply asleep where such events do not occur, and furthermore, the false pressure increments become smaller with repeated events. Once the subject reaches deeper sleep, any such falsely increased pressure will diminish. However, it is still advantageous to avoid falsely or needlessly increasing pressure in response to such sleep onset open airway apneas.

As previously discussed, one prior art method for avoiding unnecessary increases in pressure in response to open airway apneas is to determine the conductance of the airway during an apnea using the forced oscillation method, and only increase mask pressure if the conductance is less than a threshold. However, if the nasal airway is narrow or if the subject has lung disease, the airway conductance may be low even in the presence of an open airway and the forced oscillation method may still falsely increase pressure in response to open airway apneas. Conversely, the combination of the forced oscillation method with embodiments of the present invention has the added advantage that in most cases open airway apneas are correctly detected by the 'forced oscillation method', but in those cases where the forced oscillation method falsely reports a closed airway, the mask pressure will not increase above 10 cmH.sub.2O, thus preventing run-away increases in pressure. This is demonstrated in a third embodiment using the following pseudo-code:

Set apnea duration to zero
Clear "start of breath" flag
REPEAT every {fraction (1/50)} of a second
Sample mask pressure (in cmH2O), mask airflow (in L/sec), and snore (1 unit corresponds loosely to a typical snore).
Calculate mask leak as mask airflow low pass filtered with a time constant of 10 seconds.
Adjust snore signal for machine noise.
Check for presence and duration of any apnea.
IF apnea in progress:
measure conductance of airway using forced oscillation method.
END
Check for start of breath.
IF start of breath flag set:
IF apnea duration greater than 10 seconds AND current CPAP pressure less than 10 cmH.sub.2O AND airway conductance measured using forced oscillation method is less than 0.05 cmH.sub.2O/L/sec:
Set delta pressure for this apnea to (10−current CPAP pressure)/6 times 8 cmH.sub.2O per minute of apnea duration.
Add delta pressure for this apnea to total delta pressure due to apnea, and truncate to 16 cmH.sub.9O
Reset apnea duration to zero.
ELSE
Reduce total delta pressure due to apnea with a time constant of 20 minutes.
END
Calculate flow limitation index.
Calculate flow limitation threshold.
IF flow limitation index is less than said threshold:
Set flow limitation delta pressure for this breath to 3 cmH.sub.2O times (threshold-flow limitation index).
Add flow limitation delta pressure for this breath to total delta pressure due to flow limitation, and truncate to 16 cmH.sub.2O.
ELSE
Reduce total delta pressure due to flow limitation with a time constant of 10 minutes.
END
Calculate mean snore for breath.
Calculate snore threshold.
IF mean snore exceeds said threshold:
set delta pressure due to snore for this breath to 3 cmH.sub.2O times (mean snore for this breath—threshold).
Add delta pressure due to snore for this breath to total delta pressure due to snore, and truncate to 16 cmH.sub.2O.
ELSE
Reduce total delta pressure due to snore with a time constant of 10 minutes.
END
Set CPAP pressure to 4 cmH.sub.2O plus total delta pressure due to apnea plus total delta pressure due to snore plus total delta pressure due to flow limitation, and truncate to 20 cmH.sub.2O.
Clear start of breath flag.
END
END
The procedure, "measure airway conductance using the forced oscillation method" can be implemented using the following pseudocode:
Modulate airway pressure with an amplitude of 1 cmH.sub.2O peak to peak at 4 Hz.
Measure amplitude of airflow signal at 4 Hz.
Measure component of mask pressure signal at 4 Hz.
Set conductance equal to said airflow amplitude divided by said mask pressure amplitude.

An alternate expression of the combination of an embodiment of the invention and the forced oscillation method is:
IF
(a) the current pressure is low AND (b) the alternative method scores the airway as closed, THEN score the airway as closed.
ELSE IF
(a) the current pressure is high AND (b) the alternative method scores the airway as open, THEN score the airway as open.
ELSE
score the apnea as of unknown type.
A further possible arrangement is to substitute the 'cardiogenic method' for determining airway patency for the 'forced oscillation method', also disclosed in European Publication No. 0 651 971 A1 (and U.S. Pat. No. 5,704,345).
More complex variants of CPAP therapy, such as bi-level CPAP therapy or therapy in which the mask pressure is modulated within a breath, can also be monitored and/or controlled using the methods described herein.

We claim:

1. A Continuous Positive Airway Pressure device that detects flow limitations and apneas of a patient under treatment during sleep and in response thereto auto-adjusts the treatment pressure comprising:
a breathing tube connectable to a mask for delivery of a supply of air or breathable gas at a treatment pressure to an entrance of the patient's airway;
a motor driven blower adapted to provide the supply of air or breathable gas to the breathing tube at a controllable pressure;
a flow sensor arranged to determine a flow of air to the patient;
a controller adapted to detect flow limitations and apneas from said flow signal, and being further adapted to control the treatment pressure in accordance with an auto-adjusting algorithm;
the auto-adjusting algorithm being characterized in that:
the treatment pressure has a range defined by a minimum pressure and a maximum pressure; and
in response to flow limitations, the treatment pressure is increased to a pressure no higher than the maximum pressure; and
in response to apneas, the treatment pressure is increased to a pressure no higher than an apnea cap pressure, wherein the apnea cap pressure is a pressure that is less than the maximum pressure.

2. The device of claim 1 wherein the minimum pressure is about 4 cmH$_2$O.

3. The device of claim 1 wherein the apnea cap pressure is about 10 cmH$_2$O.

4. The device of claim 1 wherein the maximum pressure is about 20 cmH$_2$O.

5. The device of claim 1 used for treatment of Obstructive Sleep Apnea or Upper Airway Resistance syndrome.

6. The device of claim 1 wherein the auto-adjusting algorithm is further characterized in that the treatment pressure is reduced towards the minimum pressure if apnea is not detected.

7. The device of claim 1 wherein the auto-adjusting algorithm is further characterized in that the treatment pressure is reduced towards the minimum pressure if flow limitation is not detected.

8. The device of claim 1 wherein the auto-adjusting algorithm is further characterized in that the treatment pressure is reduced towards the minimum pressure if apnea and flow limitation are not detected.

9. The device of claim 1 wherein the auto-adjusting algorithm is further characterized in that an increment in pressure in response to an apnea when the treatment pressure is close to the apnea cap pressure is smaller than an increment in pressure in response to an apnea when the treatment pressure is close to the minimum pressure.

10. The device of claim 1 wherein the auto-adjusting algorithm includes a leak compensation procedure.

11. The device of claim 10 wherein the leak compensation procedure comprises adjusting the flow limitation threshold if there is a large leak.

12. The device of claims 1 further adapted to distinguish open airway apneas and closed airway apneas using forced oscillation.

* * * * *